United States Patent [19]

Raghu et al.

[11] 4,339,603

[45] Jul. 13, 1982

[54] PROCESS FOR CONVERTING OPTICALLY ACTIVE L-N-(2-AMINO-2-PHENETHYL)-2-METHOXYETHYLAMINE TO THE CORRESPONDING DL-DERIVATIVE

[75] Inventors: Sivaraman Raghu, Norwalk; Arnold Zweig, Westport, both of Conn.

[73] Assignee: American Cyanamid Company, Stamford, Conn.

[21] Appl. No.: 1,807

[22] Filed: Jan. 8, 1979

[51] Int. Cl.$^3$ .................................................. C07C 20/00
[52] U.S. Cl. .............................. 564/302; 260/571.1; 548/351; 564/220; 564/372
[58] Field of Search ................ 260/571.5 P; 564/302

[56] References Cited

U.S. PATENT DOCUMENTS

| | | | |
|---|---|---|---|
| 2,514,380 | 7/1950 | Duschinsky | 260/570.5 X |
| 3,184,460 | 5/1965 | Akkerman et al. | 260/570.5 X |
| 3,845,070 | 10/1974 | McMenim | 260/570.5 X |
| 3,923,808 | 12/1975 | Gelder et al. | 260/570.5 X |

*Primary Examiner*—Robert V. Hines
*Attorney, Agent, or Firm*—Gordon L. Hart

[57] ABSTRACT

There is provided a process for racemizing an undesirable, optically active compound for conversion to levamisole, namely, l-N-(2-amino-2-phenethyl)-2-methoxyethylamine, by converting the latter to optically active l-(2-methoxyethyl)-4-phenyl-2-imidazolidone, which is next converted to the corresponding optically inactive imidazolidone derivative, which derivative is hydrolyzed to the optically inactive racemate, dl-N-(2-amino-2-phenethyl)-2-methoxyethylamine. The latter can be resolved to obtain the d and l components of the racemate, the d component being utilized directly in levamisole synthesis and the l component being again subjected to the above procedure.

5 Claims, No Drawings

PROCESS FOR CONVERTING OPTICALLY ACTIVE L-N-(2-AMINO-2-PHENETHYL)-2-METHOXYETHYLAMINE TO THE CORRESPONDING DL-DERIVATIVE

The present invention relates to a process for utilizing an otherwise undesirable enantiomer, optical active l-N-(2-amino-2-phenethyl)-2-methoxyethylamine, to obtain the corresponding inactive compound which is capable of being resolved. More particularly, the present invention relates to a process for utilizing optically active but undesirable l-N-(2-amino-2-phenethyl)-2-methoxyethylamine to a desirable form, namely, to the corresponding dl form by a plurality of steps involving the conversion of the l amine isomer to optically active l-(2-methoxyethyl)-4-phenyl-2-imidazolidone, which is next converted to the corresponding optically inactive imidazolidone derivative, said latter derivative being hydrolyzed to the optically inactive racemate, dl-N-(2-amino-2-phenethyl)-2-methoxyethylamine and the latter is resolved to obtain the d- and l components of the racemate, wherein the d component is utilized directly in levamisole synthesis and the l component is again subjected to the above procedure.

In a copending application of Nancy S. Kurose, Ser. No. 958,220, filed Nov. 6, 1978 and now abandoned, which is incorporated herein by reference, there is disclosed a process for resolving racemic N-(2-amino-2-phenethyl)-2-methoxyethylamine with dibenzoyl-d-tartaric acid to obtain the desirable d isomer, leaving unused the l isomer which cannot be utilized in a direct synthesis to levamisole. If a process could be provided to utilize rather than to discard the aforementioned l isomer, a long-felt need in the art would be satisfied.

It has been unexpectedly found that an undesirable optical isomer, l-N-(2-amino-2-phenethyl)-2-methoxyethylamine, can be readily converted to a more desirable form, namely, the racemate thereof. The latter is capable of being resolved to the desirable d-isomer and the remaining l-isomer is recycled for further treatment.

According to the process of the invention, an optically active compound, l-N-(2-amino-2-phenethyl)-2-methoxy-ethylamine, is initially subjected to reaction with urea to obtain l-(2-methoxyethyl)-4-phenethyl-2-imidazolidone, which is next dehydrogenated and hydrogenated employing a noble metal catalyst or an equivalent thereof to yield dl 1-(2-methoxyethyl)-4-phenyl-2-imidazolidone, then the latter is next heated with a hydrolyzing agent, such as sulfuric acid, to obtain dl-N-(2-amino-2-phenethyl)-2-methoxyethylamine which can be resolved to obtain both d and l components and, thereafter, subjecting the l component to the above treatment while utilizing the d component to effect direct synthesis to levamisole.

The hereinabove-defined optically active but undesirable l-isomer is obtained as set forth in the aforementioned copending application Ser. No. 958,220 by initially reacting styrene oxide and 2-methoxyethylamine to obtain dl-N-(2-hydroxy-2-phenethyl)-2-methoxyethylamine which in turn is reacted with acidified acetonitrile to yield dl-N-(2-acetamido-2-phenethyl)-2-methoxyethylamine. The latter is next resolved with dibenzoyl-d-tartaric acid by forming a slurried solution thereof with acidified water and ammonium chloride to recover the d-isomer as crystals and the l-isomer remains in solution. After removal of the acidified aqueous solution, there remains the undesirable l-isomer.

In general, the above overall reactions utilizing the undesirable l-isomer for the recovery of desirable racemate can be set forth in the reactions set forth below:

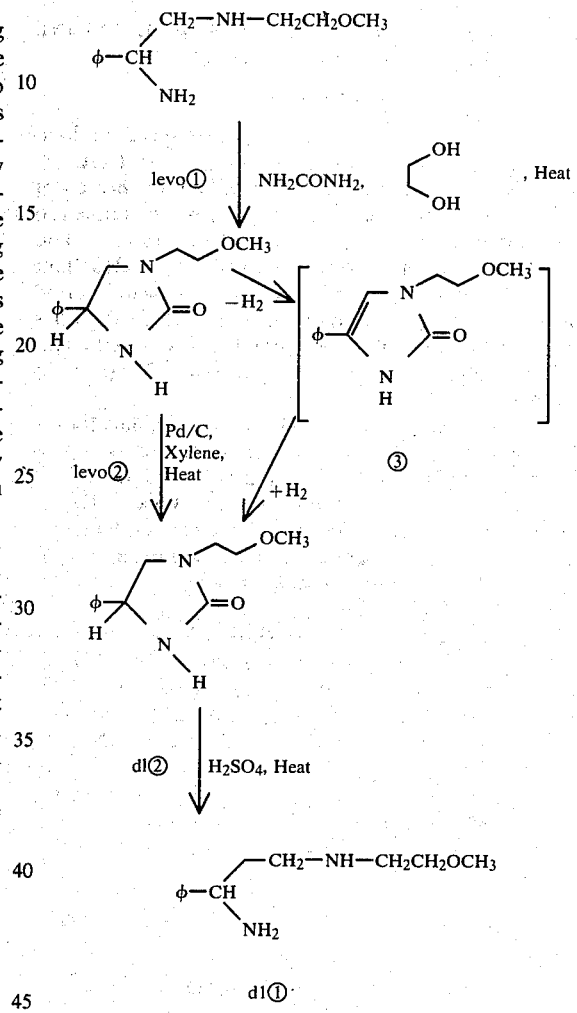

where φ is phenyl.

It will be noted from the above reaction sequence that l-N(2-amino-2-phenethyl)-2-methoxyethylamine ① is reacted with urea in equimolar amounts in the presence of a lower alkylene glycol, such as ethylene glycol or propylene glycol, at temperatures ranging from about 180° C. to about 240° C. for from about one-half to five hours. However, if desired, the glycol solvent need not be present during reaction. Resultant 1-(2-methoxyethyl)-4-phenyl-2-imidazolidone ② is subjected to dehydrogenation and hydrogenation by heating the same, for instance, in a closed reaction vessel with palladium on carbon in the presence of xylene usually at temperatures ranging between 100° C. and 170° C. for from one hour to twenty-four hours, whereby racemization is effected to obtain intermediate 1-(2-methoxyethyl)-4-phenyl-imidazolin-2-one ③ which then is converted in situ to dl 1-(2-methoxyethyl)-4-phenyl-2-imidazolidone ②. Alternatively, the optically active l-1-(2-methoxyethyl)-4-phenyl-2-imidazolidone ② is initially dehydrogenated in an open vessel to 1-(2-methoxyethyl)-4-phenyl-4-imidazolin-2-one ③ and the latter is then hydrogenated to dl 1-(2-methoxyethyl)-4-phenyl-2-imidazolidone ②. The latter is thereafter hydrolyzed to racemic N-(2-amino-2-phenethyl)-2-methoxyethylamine ① by heating dl imidazolidone ② with an aqueous mineral acid, such as sulfuric acid in a concentration usually ranging between 50% and 70%.

The following non-limiting example is incorporated herein to further illustrate the invention.

EXAMPLE 1

A mixture of 1-N-(2-amino 2-phenylethyl)-2-methoxyethylamine [7.8 gm, $[\alpha]_D^{20} = -32(c=1$ in $CHCl_3)$], urea (3.0 gm) and ethyleneglycol (1 gm) is heated at 210°–215° C. for 3 hours. The mixture is then cooled to room temperature, and a mixture of 50 gm of water and 50 ml of methylenechloride is then added. Resultant organic layer is separated, washed with water, dried and solvent is removed to obtain an oil which solidifies on standing. The latter is identified as l-1-(2-methoxyethyl)-4-phenyl-2-imidazolidone, $[\alpha]_D^{20} = -31.5(c=1$ in $CHCl_3)$.

The l-1-(2-methoxyethyl)-4-phenyl-2-imidazolidone (7.5 g) so obtained is admixed with xylene and 10% palladium on charcoal (0.7 g) and is heated at 150° C. under 20–50 psig nitrogen pressure for 24 hours. Resultant mixture is then cooled; next, catalyst is filtered off and the filtrate is concentrated to provide racemic 1-(2-methoxyethyl)-4-phenyl-2-imidazolidone, $[\alpha]_D^{20} = -0.2$, (c=1, $CHCl_3$).

The racemic 1-(2-methoxyethyl)-4-phenyl-2-imidazolidone (2.2 g) obtained is heated at 140°–150° C. for 20 hours with 60 weight percent sulfuric acid. The solution is cooed to room temperature, diluted with water and 20% potassium hydroxide to attain a pH of 10 and extracted with methylene chloride. The extracts are washed, dried and concentrated to yield racemic N-(2-amino-2-phenylethyl)-2-methoxyethylamine, $[\alpha]_D^{20} = -0.00$ (c=1, $CHCl_3$).

EXAMPLE 2

Dehydrogenation of Optically Active Imidazolidone

In a suitable reaction vessel are admixed l-1-(2-methoxyethyl)-4-phenyl-2-imidazolidone (6.8 gm), $[\alpha]_D^{20} = -31(c=1$ in $CHCl_3)$ and 10 percent palladium on charcoal (0.7 gm) in xylene and then refluxed for 6 hours. The catalyst is filtered while still hot and washed with hot xylene. The combined filtrate is concentrated to yield a solid identified by infrared (IR) and NMR spectroscopy as 1-(2-methoxyethyl)-4-phenyl-4-imidazolin-2-one (6.5 g).

The 1-(2-methoxyethyl)-4-phenyl-4-imidazolin-2-one (6.5 g) so obtained is next admixed with 10% palladium on carbon (0.7 g) in ethanol (50 ml). The mixture is thereafter hydrogenated at 50 psi at room temperature for four hours and the catalyst is filtered. Resultant filtrate is finally concentrated to yield racemic 1-(2-methoxyethyl)-4-phenyl-2-imidazolidone (6.0 g), $[\alpha]_D^{20} = -0.2(c=1$ in $CHCl_3)$.

We claim:
1. A process for the racemization of optically active l-N-(2-amino-2-phenethyl)-2-methoxyethylamine which comprises the steps of:
    (a) converting optically active l-N-(2 amino-2-phenethyl)-2-methoxyethylamine to optically active l-1-(2-methoxyethyl)-4-phenyl-2-imidazolidone,
    (b) subjecting the latter optically active imidazolidone to dehydrogenation and hydrogenation to obtain optically inactive, racemic (dl) 1-(2-methoxyethyl)-4-phenyl-2-imidazolidone,
    (c) converting the latter racemic imidazolidone by acid hydrolysis, and
    (d) recovering optically inactive, racemic dl N-(2-amino-2-phenethyl)-2-methoxyethylamine.
2. The process according to claim 1 wherein step (b) is carried out in the presence of palladium catalyst on carbon.
3. The process according to claim 2 wherein the reaction is carried out in a closed reaction vessel.
4. The process according to claim 1, wherein optically active levo 1-(2-methoxyethyl)-4-phenyl-2-imidazolidone is first dehydrogenated to 1-(2-methoxyethyl)-4-phenyl-4-imidazolin-2-one, and the latter is then hydrogenated to racemic 1-(2-methoxyethyl)-4-phenyl-2-imidazolidone.
5. The process according to claim 1, wherein in step (d) thereof, the acid is sulfuric acid.

* * * * *